United States Patent
O'Brien et al.

(10) Patent No.: US 7,854,172 B2
(45) Date of Patent: Dec. 21, 2010

(54) HERMETIC CHAMBER WITH ELECTRICAL FEEDTHROUGHS

(75) Inventors: David O'Brien, Norcross, GA (US); Florent Cros, Decatur, GA (US); Jin Woo Park, Suwanee, GA (US); Michael Fonseca, Marietta, GA (US); Liang You, Alpharetta, GA (US); Mark Allen, Atlanta, GA (US)

(73) Assignee: CardioMEMS, Inc., Atlanta, GA (US)

( * ) Notice: Subject to any disclaimer, the term of this patent is extended or adjusted under 35 U.S.C. 154(b) by 83 days.

(21) Appl. No.: 12/372,274

(22) Filed: Feb. 17, 2009

(65) Prior Publication Data

US 2009/0145623 A1    Jun. 11, 2009

(51) Int. Cl.
*G01L 7/00* (2006.01)

(52) U.S. Cl. ........................................ 73/756

(58) Field of Classification Search ........................ None
See application file for complete search history.

(56) References Cited

U.S. PATENT DOCUMENTS

| | | | |
|---|---|---|---|
| 2,769,863 A | 6/1957 | Von Wittern |
| 3,867,950 A | 2/1975 | Fischell |
| 3,942,382 A | 3/1976 | Hok |
| 3,958,558 A | 5/1976 | Dunphy et al. |
| 4,026,276 A | 5/1977 | Chubbuck |
| 4,127,110 A | 11/1978 | Bullara |
| 4,206,762 A | 6/1980 | Cosman |
| 4,207,604 A | 6/1980 | Bell |
| 4,207,903 A | 6/1980 | O'Neil |
| RE30,366 E | 8/1980 | Rasor |
| 4,237,900 A | 12/1980 | Schulman et al. |
| 4,354,506 A | 10/1982 | Sakaguchi et al. |
| 4,378,809 A | 4/1983 | Cosman |
| 4,485,813 A | 12/1984 | Anderson et al. |
| 4,494,950 A | 1/1985 | Fischell |
| 4,521,684 A | 6/1985 | Gilby et al. |

(Continued)

FOREIGN PATENT DOCUMENTS

CA    1158061    6/1983

(Continued)

OTHER PUBLICATIONS

"Helix", *The American Heritage Dictionary of the English Language.* Boston, MA: *Houghton Mifflin* http://www.credoreference.com/entry/7055911 Aug. 21, 2008.

(Continued)

*Primary Examiner*—Andre J Allen
(74) *Attorney, Agent, or Firm*—Ballard Spahr LLP

(57) ABSTRACT

A pressure cavity is durable, stable, and biocompatible and configured in such a way that it constitutes pico to nanoliter-scale volume. The pressure cavity is hermetically sealed from the exterior environment while maintaining the ability to communicate with other devices. Micromachined, hermetically-sealed sensors are configured to receive power and return information through direct electrical contact with external electronics. The pressure cavity and sensor components disposed therein are hermetically sealed from the ambient in order to reduce drift and instability within the sensor. The sensor is designed for harsh and biological environments, e.g. intracorporeal implantation and in vivo use. Additionally, novel manufacturing methods are employed to construct the sensors.

33 Claims, 9 Drawing Sheets

U.S. PATENT DOCUMENTS

| | | | |
|---|---|---|---|
| 4,596,563 A | 6/1986 | Pande | |
| 4,617,606 A | 10/1986 | Shak et al. | |
| 4,701,826 A | 10/1987 | Mikkor | |
| 4,713,540 A | 12/1987 | Gilby et al. | |
| 4,718,425 A | 1/1988 | Tanaka et al. | |
| 4,773,972 A | 9/1988 | Mikkor | |
| 4,796,641 A | 1/1989 | Mills et al. | |
| 4,815,472 A | 3/1989 | Wise et al. | |
| 4,846,191 A | 7/1989 | Brockway et al. | |
| 4,890,623 A | 1/1990 | Cook et al. | |
| 4,899,752 A | 2/1990 | Cohen | |
| 4,913,147 A | 4/1990 | Fahlstrom et al. | |
| 4,924,172 A | 5/1990 | Holmgren | |
| 4,934,369 A | 6/1990 | Maxwell | |
| 4,987,897 A | 1/1991 | Funke | |
| 5,036,854 A | 8/1991 | Schollmeyer et al. | |
| 5,113,868 A | 5/1992 | Wise et al. | |
| 5,115,128 A | 5/1992 | Cook | |
| 5,129,394 A | 7/1992 | Mehra | |
| 5,165,289 A | 11/1992 | Tilmans | |
| 5,173,836 A | 12/1992 | Tomase et al. | |
| 5,181,423 A | 1/1993 | Philipps et al. | |
| 5,192,314 A | 3/1993 | Daskalakis | |
| 5,207,103 A | 5/1993 | Wise et al. | |
| 5,265,606 A | 11/1993 | Kujawski | |
| 5,277,068 A | 1/1994 | Fukiura et al. | |
| 5,353,800 A | 10/1994 | Pohndorf et al. | |
| 5,355,714 A | 10/1994 | Suzuki et al. | |
| 5,373,852 A | 12/1994 | Harrison et al. | |
| 5,400,535 A | 3/1995 | Schomaker | |
| 5,411,535 A | 5/1995 | Fujii et al. | |
| 5,431,171 A | 7/1995 | Harrison et al. | |
| 5,440,300 A | 8/1995 | Spillman, Jr. | |
| 5,487,760 A | 1/1996 | Villafana | |
| 5,497,099 A | 3/1996 | Walton | |
| 5,515,041 A | 5/1996 | Spillman, Jr. | |
| 5,535,752 A | 7/1996 | Halperin et al. | |
| 5,538,005 A | 7/1996 | Harrison et al. | |
| 5,551,427 A | 9/1996 | Altman | |
| 5,554,139 A | 9/1996 | Okajima | |
| 5,566,676 A | 10/1996 | Rosenfeldt et al. | |
| 5,593,430 A | 1/1997 | Renger | |
| 5,600,245 A | 2/1997 | Yamamoto et al. | |
| 5,626,630 A | 5/1997 | Markowitz et al. | |
| 5,686,841 A | 11/1997 | Stolarczyk et al. | |
| 5,695,155 A | 12/1997 | Macdonald et al. | |
| 5,702,427 A | 12/1997 | Ecker et al. | |
| 5,703,576 A | 12/1997 | Spillman, Jr. et al. | |
| 5,713,917 A | 2/1998 | Leonhardt et al. | |
| 5,722,414 A | 3/1998 | Archibald et al. | |
| 5,723,791 A | 3/1998 | Koch et al. | |
| 5,740,594 A | 4/1998 | Lukasiewicz et al. | |
| 5,743,267 A | 4/1998 | Nikolic et al. | |
| 5,750,926 A | 5/1998 | Schulman et al. | |
| 5,796,827 A | 8/1998 | Coppersmith et al. | |
| 5,807,265 A | 9/1998 | Itoigawa et al. | |
| 5,836,886 A | 11/1998 | Itoigawa et al. | |
| 5,860,938 A | 1/1999 | Lafontaine et al. | |
| 5,899,927 A | 5/1999 | Ecker et al. | |
| 5,935,084 A | 8/1999 | Southworth | |
| 5,942,991 A | 8/1999 | Gaudreau et al. | |
| 5,967,986 A | 10/1999 | Cimochowski et al. | |
| 5,974,894 A | 11/1999 | Delatorre | |
| 6,015,386 A | 1/2000 | Kensey et al. | |
| 6,015,387 A | 1/2000 | Schwartz et al. | |
| 6,019,729 A | 2/2000 | Itoigawa et al. | |
| 6,024,704 A | 2/2000 | Meador et al. | |
| 6,025,725 A | 2/2000 | Gershenfeld et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Geierbach | |
| 6,111,520 A | 8/2000 | Allen et al. | |
| 6,113,553 A | 9/2000 | Chubbuck | |
| 6,134,461 A | 10/2000 | Say et al. | |
| 6,140,740 A | 10/2000 | Porat et al. | |
| 6,159,156 A | 12/2000 | Van Bockel | |
| 6,198,965 B1 | 3/2001 | Penner et al. | |
| 6,201,980 B1 | 3/2001 | Darrow et al. | |
| 6,206,835 B1 | 3/2001 | Spillman, Jr. et al. | |
| 6,212,056 B1 | 4/2001 | Gammel et al. | |
| 6,237,398 B1 | 5/2001 | Porat et al. | |
| 6,239,724 B1 | 5/2001 | Doron et al. | |
| 6,252,481 B1 | 6/2001 | Iwao et al. | |
| 6,277,078 B1 | 8/2001 | Porat et al. | |
| 6,278,379 B1 | 8/2001 | Allen et al. | |
| 6,287,253 B1 | 9/2001 | Ortega et al. | |
| 6,291,343 B1 | 9/2001 | Tseng et al. | |
| 6,338,284 B1 | 1/2002 | Najafi et al. | |
| 6,373,264 B1 | 4/2002 | Matsumoto et al. | |
| 6,383,144 B1 | 5/2002 | Mooney et al. | |
| 6,409,674 B1 | 6/2002 | Brockway et al. | |
| 6,416,474 B1 | 7/2002 | Penner et al. | |
| 6,442,413 B1 | 8/2002 | Silver | |
| 6,454,720 B1 | 9/2002 | Clerc et al. | |
| 6,645,143 B2 | 11/2003 | Van Tassel et al. | |
| 6,667,725 B1 | 12/2003 | Simmons et al. | |
| 6,678,458 B2 | 1/2004 | Ellis et al. | |
| 6,689,056 B1 | 2/2004 | Kilcoyne et al. | |
| 6,765,493 B2 | 7/2004 | Lonsdale et al. | |
| 6,812,404 B1 | 11/2004 | Martinez | |
| 6,855,115 B2 | 2/2005 | Fonseca et al. | |
| 6,923,769 B2 | 8/2005 | Nishii et al. | |
| 6,926,670 B2 | 8/2005 | Rich et al. | |
| 6,939,299 B1 | 9/2005 | Petersen et al. | |
| 6,989,493 B2 | 1/2006 | Hipwell et al. | |
| 7,119,552 B2 | 10/2006 | Morimoto et al. | |
| 7,147,604 B1 | 12/2006 | Allen et al. | |
| 7,647,836 B2 * | 1/2010 | O'Brien et al. | ............... 73/756 |
| 2001/0001311 A1 | 5/2001 | Park et al. | |
| 2002/0013994 A1 | 2/2002 | Ahn | |
| 2002/0151816 A1 | 10/2002 | Rich et al. | |
| 2002/0170897 A1 | 11/2002 | Hall | |
| 2002/0188207 A1 | 12/2002 | Richter | |
| 2003/0031587 A1 | 2/2003 | Hu et al. | |
| 2003/0125790 A1 | 7/2003 | Fastovsky et al. | |
| 2003/0136417 A1 | 7/2003 | Fonseca et al. | |
| 2003/0139677 A1 | 7/2003 | Fonseca et al. | |
| 2003/0143775 A1 | 7/2003 | Brady | |
| 2003/0219220 A1 | 11/2003 | Ellis et al. | |
| 2004/0059348 A1 | 3/2004 | Geske et al. | |
| 2004/0073137 A1 | 4/2004 | Lloyd et al. | |
| 2004/0077117 A1 | 4/2004 | Ding et al. | |
| 2004/0122494 A1 | 6/2004 | Eggers et al. | |
| 2004/0157367 A1 | 8/2004 | Wong et al. | |
| 2004/0176672 A1 | 9/2004 | Silver et al. | |
| 2005/0075697 A1 | 4/2005 | Olson et al. | |
| 2005/0085703 A1 | 4/2005 | Behm | |
| 2005/0154321 A1 | 7/2005 | Wolinsky et al. | |
| 2005/0187482 A1 | 8/2005 | O'Brien et al. | |
| 2005/0194174 A1 | 9/2005 | Hipwell et al. | |
| 2005/0229710 A1 | 10/2005 | O'Dowd et al. | |
| 2006/0129056 A1 | 6/2006 | Leuthardt et al. | |
| 2006/0174712 A1 * | 8/2006 | O'Brien et al. | ............... 73/756 |
| 2006/0177956 A1 | 8/2006 | O'Brien et al. | |
| 2006/0241354 A1 | 10/2006 | Allen | |
| 2006/0283007 A1 | 12/2006 | Cros et al. | |
| 2006/0287602 A1 | 12/2006 | O'Brien et al. | |
| 2006/0287700 A1 | 12/2006 | White et al. | |

| | | | |
|---|---|---|---|
| 2007/0107524 A1* | 5/2007 | O'Brien et al. | 73/754 |
| 2007/0199385 A1* | 8/2007 | O'Brien et al. | 73/718 |
| 2007/0261497 A1* | 11/2007 | O'Brien et al. | 73/724 |
| 2008/0060834 A1 | 3/2008 | Eck et al. | |
| 2008/0060844 A1 | 3/2008 | Teske et al. | |

FOREIGN PATENT DOCUMENTS

| | | |
|---|---|---|
| DE | 19644858.5 | 10/1996 |
| DE | 10052053 A1 | 4/2002 |
| DE | 10135568 | 2/2003 |
| EP | 0337035 | 11/1993 |
| EP | 0646365 | 4/1995 |
| WO | WO 83/03348 | 10/1983 |
| WO | WO90/06723 | 6/1990 |
| WO | WO 93/08871 | 5/1993 |
| WO | WO 95/33517 | 12/1995 |
| WO | WO 97/09926 | 3/1997 |
| WO | WO 97/32518 | 9/1997 |
| WO | WO 97/33513 | 9/1997 |
| WO | WO 97/35219 | 9/1997 |
| WO | WO 98/47727 | 10/1998 |
| WO | WO 99/34731 | 7/1999 |
| WO | WO 00/16686 | 3/2000 |
| WO | WO 01/00089 | 1/2001 |
| WO | WO 01/87137 | 11/2001 |
| WO | WO 01/97908 | 12/2001 |
| WO | WO 03/061504 | 7/2003 |
| WO | WO 03/106952 | 12/2003 |
| WO | WO 2004/014456 | 2/2004 |
| WO | WO 2004/098701 | 11/2004 |
| WO | WO 2005/019785 A | 3/2005 |
| WO | WO-2005027998 A2 | 3/2005 |
| WO | WO 2006/086113 | 8/2006 |
| WO | WO 2006/086114 | 8/2006 |
| WO | WO 2007/002185 | 1/2007 |
| WO | WO 2007/002224 | 1/2007 |
| WO | WO 2007/002225 | 1/2007 |
| WO | WO 2007/047571 A | 4/2007 |
| WO | WO 2007/047794 A | 4/2007 |

OTHER PUBLICATIONS

"Interefere", *The American Heritage Dictionary of the English Language*. Boston, MA: *Houghton Mifflin* http://www.credoreference.com/entry/7072413 Aug. 22, 2008.

"Spiral", *The American Heritage Dictionary of the English Language*. Boston, MA: *Houghton Mifflin* http://www.credoreference.com/entry/7129585 Aug. 21, 2008.

Adams, Jr., K. F. "Guiding Heart Failure Care by Invasive Hemodynamic Measurements: Possible or Useful?", *Journal of Cardiac Failure* Apr. 2002 , vol. 8, No. 2, 71-73.

Akar, O. et al., "A Wireless Batch Sealed Absolute Capacitive Pressure Sensor", *Sensor and Actuators* Dec. 15, 2001 , 95(1), 29-38.

Akin, T. et al., "RF Telemetry Powering and Controlling of Hermetically Sealed Integrated Sensors and Actuators", *Center for Integrated Sensors and Circuits; Department of Electrical Engineering and Computer Science*; University of Michigan; Ann Arbor, Michigan 48109-2122 , 145-148.

Akingba, G. et al., "An Implantable Pressure Sensor for Aneurysmal Disease", Admitted Prior Art.

Baum, R. A. et al., "Aneurysm Sac Pressure Measurements After Endovascular Repair of Abdominal Aortic Aneurysms", *Journal of Vascular Surgery* , vol. 33, No. 1, Jan. 2001, 32-41.

Chuter, T. et al., "Endovascular and Surgical Techniques", *Eur J. Vasc Endovasc Surg* Jan. 1997 , vol. 13, 85-87.

Dehennis, A. et al., "A Double-Sided Single-Chip Wireless Pressure Sensor", Dig. IEEE MEMS Conf., Jan. 2002, pp. 252-255.

Dehennis, A. et al., "A Passive-Telemetry-Based Pressure Sensing System", Proc. Solid State Sensors and Actuators Workshop, Hilton Head, SC, 2002, pp. 165-168.

Farrar, J. T. et al., "Telemetering of Intraenteric Pressure In Man By An Externally Energized Wireless Capsule", *Science* Jun. 17, 1960 , New Series, vol. 131, Issue 3416, 1814.

Gawenda, M. et al., "Intra-Aneurysm Sac Pressure-The Holy Gail of Endoluminal Grafting of AAA", *Eur J Vasc Endovasc Surg* Aug. 2002 , vol. 24, 139-145.

Gawenda, M. et al., "Pressure if Transmitted Through PTFE and Dacron Grafts Leading the Aneurysm Sac Pressure Endoluminal Grafting of AAA—An In Vitro Study", Vascular Centre, University of Cologne, Germany, Admitted Prior Art.

Harris, P. L. et al., "Predicting Failure of Endovascular Aneurysm Repair", Eur J Vas Endovasc Surg Jan. 1999 , vol. 17, 1-2.

Haynes, H. E. et al., "Medical Electronics: The Pill That Talks", DEP, Camden, N.J., RCE Engineer, vol. 5, Feb.-Mar. 1960.

Magalski, A. et al., "Continuous Ambulatory Right Heart Pressure Measurements With an Implantable Hemodynamic Monitor: A Multicenter, 12-Month Follow-Up Study of Patients With Chronic Heart Failure", Journal of Cardiac Failure Apr. 2002 , vol. 8, 63-70.

Manwaring, M. L. et al., "Remote Monitoring of Intercranial Pressure", Institute of Concology; Annals of the Academy of Studencia Apr. 2001 , 77-80.

Ouriel, K. "Role of Intrasac Pressure Measurements After EVAR: Can They Be Followed Noninvasively?", Combined Session: Vascular Surgery and Interventional Radiology, VII 4.1, VEITH Meeting, New York, 2001.

Parodi, J. C. et al., "Intra-Eneurysmal Pressure After Incomplete Endovascular Exclusion", Journal of Vascular Surgery Nov. 2001 , vol. 24, No. 5, 909-914.

Schurink, Gwh et al., "Endoleakage After Stent-Graft Treatment of Abdominal Aneurysm: Implications On Pressure and Imaging-An In Vitro Study", Journal of Vascular Surgery , vol. 28, No. 2, 234-241.

Schurink, Gwh et al., "Experimental Study of the Influence of Endoleakage Size on Pressure in the Aneurysm Sac and the Consequences of Thrombosis", British Journal of Surgery 2002 , 87:71-78.

Shabetai, R. "Monitoring Heart Failure Hemodynamics With an Implanted Device: Its Potential to Improve Outcome", Journal of the American College of Cardiology Feb. 19, 2003 , vol. 41, No. 4, 572-573.

Skillern, C. S. et al., "Endotension In An Experimental Aneurysm Model", Journal of Vascular Surgery Oct. 2002 , vol. 36, No. 4, 814-817.

Sonesson, B. et al., "Intra-Aneurysm Pressure Measurements in Successfully Excluded Abdominal Aortic Aneurysm After Endovascular Repair in the Absence of Graft-Related Endoleak", Journal of Vascular Surgery Apr. 2003 , vol. 37, 773-738.

Sonesson, B. et al., "Intra-Aneurysm Pressure Measurements in Successfuly Excluded Abdominal Aortic Aneurysm After Endovascular Repair", Journal of Vascular Surgery Apr. 2003 , vol. 37, No. 4, 733-738.

Treharne, G. D. et al., "Quality Control During Endovascular Aneurysm Repair: Monitoring Aneurysmal Sac Pressure and Superficial Femoral Artery Flow Velocity", J. Endovasc Surg. 1999 , 6:239-245.

Vallabhanenia, S. R. et al., "Aortic Side Branch Perfusion Alone Does Not Account for High Intra-Sac Pressure After Endovascular Repair (EVAR) in the Absence of Graft-Related Endoleak", European Journal of Vascular and Endovascular Surgery, vol. 25, Issue 4, pp. 354-359, Mar. 15, 2003.

Zhe, J. et al., "A MEMS Device for Measurement of Skin Friction With Capacitive Sensing", Proc. Of IEEE MEMS, 2001.

* cited by examiner

HERMETIC CHAMBER WITH ELECTRICAL FEEDTHROUGHS

CROSS-REFERENCE TO RELATED APPLICATIONS

This application is entitled to the filing dates of provisional U.S. Patent Application Ser. No. 60/651,670, filed Feb. 10, 2005, provisional U.S. Patent Application Ser. No. 60/653,868, filed Feb. 17, 2005, and non-provisional U.S. patent application Ser. No. 11/314,046, filed Dec. 20, 2005, now abandoned.

BACKGROUND OF THE INVENTION

1. Field of the Invention

The present invention relates to micromachinable, pico- to nanoliter-volume, hermetic packaging that incorporates reliable electrical feedthroughs, and sensors configured utilizing the same, all of which are intended to perform reliably in harsh and biological environments.

2. Description of the Prior Art

Over the past 20 years, advances in the field of microelectronics have enabled the realization of microelectromechanical systems (MEMS) and corresponding batch fabrication techniques. These developments have allowed the creation of sensors and actuators with micrometer-scale features. With the advent of the above-described capability, heretofore implausible applications for sensors and actuators are now significantly closer to commercial realization.

In parallel, much work has been done in the development of pressure sensors. Pressure sensors are disclosed, for example, in U.S. Pat. No. 6,855,115, issued Feb. 15, 2005; U.S. patent application Ser. No. 10/054,671, filed Jan. 22, 2002; U.S. patent application Ser. No. 10/215,377, filed Aug. 7, 2002; U.S. patent application Ser. No. 10/215,379, filed Aug. 7, 2002; U.S. patent application Ser. No. 10/943,772, filed Sep. 16, 2004; and U.S. patent application Ser. No. 11/157,375, filed Jun. 21, 2005, all of which are incorporated herein by reference.

In particular, absolute pressure sensors, in which the pressure external to the sensor is read with respect to an internal pressure reference, are of interest. The internal pressure reference is a volume within the sensor, sealed, which typically contains a number of moles of gas (the number can also be zero, i.e. the pressure reference can be a vacuum, which can be of interest to reduce temperature sensitivity of the pressure reference as known in the art). The external pressure is then read relative to this constant and known internal pressure reference, resulting in measurement of the external absolute pressure. For stability of the pressure reference and assuming the temperature and volume of the reference are invariant or substantially invariant, it is desirable that the number of moles of fluid inside the reference does not change. One method to approach this condition is for the reference volume to be hermetic.

The term hermetic is generally defined as meaning "being airtight or impervious to air." In reality, however, all materials are, to a greater or lesser extent, permeable, and hence specifications must define acceptable levels of hermeticity. An acceptable level of hermeticity is therefore a rate of fluid ingress or egress that changes the pressure in the internal reference volume (a.k.a. pressure chamber) by an amount preferably less than 10 percent of the external pressure being sensed, more preferably less than 5 percent, and most preferably less than 1 percent over the accumulated time over which the measurements will be taken. In many biological applications, an acceptable pressure change in the pressure chamber is on the order of 1.5 mm Hg/year.

The pressure reference is typically interfaced with a sensing means that can sense deflections of boundaries of the pressure reference when the pressure external to the reference changes. A typical example would be bounding at least one side of the pressure reference with a deflectable diaphragm or plate and measuring the deflection of the diaphragm or plate by use of, among other techniques, a piezoresistive or a capacitance measurement. If the deflection of the diaphragm or plate is sufficiently small, the volume change of the pressure reference does not substantially offset the pressure in the pressure reference.

These approaches may require an electrical feedthrough to the hermetic environment (e.g., to contact electrodes inside the hermetic pressure reference), for connection to outside electronics to buffer or transmit the signal. Alternatively, electronics may be incorporated within the reference cavity, requiring power to be conducted into the hermetic environment. To maintain stability of the pressure reference, these seals should also be hermetic, resulting in the necessity to develop a feedthrough technology for contacts through the cavity walls. As is known in the art, such feedthrough points are typically sites for failure of hermeticity. This problem is further exacerbated when miniaturizing the sensor, since the total volume of material available for hermetic sealing shrinks proportionally and the reliability of the feedthrough is also greatly reduced. In the limit of ultraminiaturized sensors, such as those producible using microelectromechanical systems (MEMS) technology, one of the major challenges to enabling the use of such devices in applications where they are physically connected to other devices has been the creation of reliable hermetic packaging that provides feedthroughs that enable exchange of power and information with external electronics.

Design criteria for ultraminiature packaging that overcomes the aforementioned shortcomings are as follows: The packaging must exhibit long term hermeticity (on the order of the life of the sensor, which in some cases can exceed tens of years). Feedthroughs must be provided through the hermetic package that do not introduce new or unnecessary potential modes of failure. The feedthroughs will constitute a necessary material interface, but all other interfaces can and should be eliminated. In other words, the number and area of material interfaces should be minimized to reduce the potential for breach of hermeticity. The materials selected must be compatible with the processes used to fabricate the package as well as sufficiently robust to resist deleterious corrosion and biocompatible to minimize the body's immune response. Finally, the packaging should be amenable to batch fabrication.

In the past, many methods for creating such hermetic packages have been proposed. One approach used in the past to create the pressure cavity is anodic bonding to create a silicon-to-glass seal. A borosilicate glass is required for this method. Another technique utilized in the creation of hermetic packages is eutectic bonding to create a silicon to metal hermetic seal, e.g. Au to Si. Both of these bonding methods used to create the pressure cavity introduce a large area along the perimeter of the material interface of the pressure cavity package which presents opportunity for failure, e.g. through corrosion. These methods for creating the pressure cavity do not minimize the area of the material interface as is desirable. A desirable improvement to the construction of the pressure cavity would minimize the material interface to the hermetic electrical feedthroughs, and, even further, minimize the number and area of material interfaces in those feedthroughs.

Previous attempts to create hermetic feedthroughs also fall short of the above-stated requirements. Many prior art hermetic feedthroughs are too large and not amenable to the required miniaturization for pico to nanoliter volume packaging achievable by MEMS or similar approaches. Furthermore, earlier attempts to create feedthroughs in pico to nanoliter packaging are prone to corrosion because of the materials used in construction or are sufficiently complicated that they introduce more material interfaces than are necessary. A representative feedthrough approach, known as a "buried" feedthrough, is illustrated in FIGS. 1-5. One method for creating a buried feedthrough is as follows: a metal 10 is deposited onto substrate 12 in a predefined pattern, as shown in FIG. 1. An insulating layer 14 is deposited on top of the metal layer, as shown in FIG. 2, and this insulating layer 14 is polished to planarize this surface. In FIG. 3 an etchant has been used to expose the metal layer at input and output sites 16, 18 for the feedthroughs. In FIG. 4, another substrate 20 is bonded on top of this structure, forming a hermetic cavity 22. A eutectic bonding method is illustrated, which involves the use of gold deposits 24 interposed between the insulating layer 14 and the upper substrate 20 to bond the upper substrate to the insulating layer. In FIG. 5 the upper substrate 20 is machined to expose the external feedthrough 18. An electrical component can now be connected to the external feedthrough 18, whereupon electrical communication is established through metal 10 to the internal feedthrough 16 and the interior of the hermetically sealed chamber 22.

This prior art buried feedthrough suffers a number of disadvantages. First, there are numerous material interfaces: an interface 30 between the lower substrate 12 and the metal 10; an interface 32 between the metal 12 and the insulating layer 14, an interface 34 between the insulating layer 14 and the gold 24; and an interface 36 between the gold 24 and the upper substrate 20, all of which create potential paths for infusion into or effusion out of the hermetic chamber 22. The creation of this buried feedthrough also introduces increased processing steps. Further, the insulating layer material is cited as being prone to corrosion in certain environments, e.g. the human body. Corrosion issues may be further exacerbated by the application of electrical bias to metal 10 which may be required in certain applications. Thus prior art hermetic feedthroughs fall short of meeting the constraints outlined above.

Also, many prior art attempts to provide pressure sensors utilize silicon as a substrate material. If the package is implanted in vivo, silicon is not an optimal material choice. Silicon invokes an undesirable immune response over other, more inert materials such as fused silica. If silicon is used, a coating must be applied to ensure biocompatibility. Such a coating increases the package size, thereby decreasing the benefits of miniaturization, and introduces an undesirable additional processing step in the manufacture of the package.

Additionally, prior art devices commonly employ the use of borosilicate glass as part of the pressure cavity. The ions in borosilicate glass constitute an impurity in the glass. The barrier to diffusion of water decreases as the purity of glass decreases. This makes use of impure glass undesirable in such applications.

Thus a need exists for hermetic pico to nanoliter packaging with electrical feedthroughs for use in biological environments, such packaging being constructed of high-purity materials and having a reduced number and area of material interfaces.

SUMMARY OF THE INVENTION

The present invention comprises a micromachinable, hermetic, pico to nanoliter-volume pressure cavity. Such a pressure cavity utilizes high-purity materials and provides reliable electrical feedthroughs. The pressure cavity is constructed of a ceramic material and is optionally fused together so that there is no interface of material where two substrates have been joined to create a cavity. Furthermore, feedthroughs establishing electrical communication within said cavity are formed in at least one of the substrates. The feedthroughs themselves are configured in such a way that the number and area of material interfaces is minimized. Such feedthroughs constitute the only site for material interface in the sensor package, thereby decreasing the number of potential leak sites in and increasing the reliability of the hermetic package. Pressure cavities and sensors of the present invention are manufactured using microelectromechanical systems (MEMS) fabrication techniques, which allow creation of a device that is small, accurate, precise, durable, robust, biocompatible, and insensitive to changes in body chemistry or biology.

The present invention further comprises a sensor that can be incorporated into harsh and biological environments. One example of such an environment is a medical lead or catheter implanted, acutely or chronically, into the human body. The sensor is configured to measure one or more physical properties such as pressure or temperature. Communication between the sensor and another device can be established by, e.g., using wires fixed to bonding pads on the exterior of the sensor packaging that are configured so that they are in electrical contact with the hermetic feedthroughs. As another example, the hermetic electrical feedthrough can have a wire extending from the feedthrough, and contact with the pressure cavity can be accomplished via connection with this wire. Devices in electrical communication with sensors according to the present invention may be either implanted or external to the body. Sensors of this invention are sufficiently small to allow for incorporation into medical leads or catheters that are twelve French or smaller, preferably six French or smaller, without causing abrupt changes in geometry of the lead or catheter, and require minimal power to perform their intended function.

In one embodiment of the invention, a wired sensor ascending to the present invention comprises a hermetic pressure cavity. The pressure cavity further comprises a capacitor configured so that the characteristic capacitance value of the capacitor varies in response to a physical property, or changes in a physical property, of a patient. The electrodes of the capacitor are substantially planar and are arranged substantially parallel to and spaced apart from one another. The pressure cavity has at least one deflectable region in mechanical communication with at least one of the capacitor electrodes. Additionally, electrical feedthroughs are formed through the substrate defining the pressure cavity and allow for the sensor to receive power and signals, and return information to either implanted or extracorporeal external electronics.

In another embodiment of the invention, a wired sensor according to the present invention comprises a hermetic pressure cavity. The pressure cavity further comprises a Wheatstone bridge configured so that the resistance value of said bridge varies in response to a physical property, or changes in a physical property, of a patient. The pressure cavity has at least one deflectable region in mechanical communication with at least one of the resistors comprising the bridge. Additionally, electrical feedthroughs are formed through the substrate and allow for the sensor to receive power and signals, and return information to external electronics. It is a further aspect of this invention that only a portion of the Wheatstone bridge be located within the pressure cavity, the other portion being contained within external electronics.

In yet another embodiment, a wired sensor further comprises on-board (i.e., within the sensor package) electronics, e.g., a silicon chip bearing electronics. The variable capacitive or resistive element and the on-board electronics can be maintained in separate cavities in electrical communication with one another by hermetic feedthroughs formed through a middle substrate. Feedthroughs establishing electrical communication with the sensor exterior may be configured so that moisture does not affect the electronics over the life of the sensor and, optionally, are also hermetic. This configuration offers the advantage that the feedthroughs to the on-board electronics act as a redundant barrier to any potential breach of the hermeticity of the pressure cavity. Alternatively, the capacitor and on-board electronics can be contained within a single hermetic cavity. This configuration offers the advantage of decreased manufacturing steps, thereby lowering the overall cost to produce the sensor. In either case, electrical feedthroughs, which are themselves optionally hermetic, formed through the substrates comprising the external walls allow for the sensor to receive power and return information to external electronics.

DETAILED DESCRIPTION OF THE INVENTION

Figure 1:
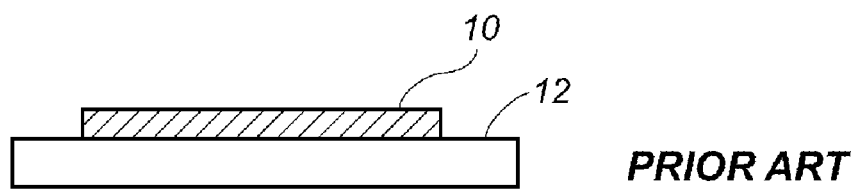
FIG. 1 is a schematic representation of a first step in manufacturing a PRIOR ART hermetic chamber with electrical feedthroughs.
Figure 2:
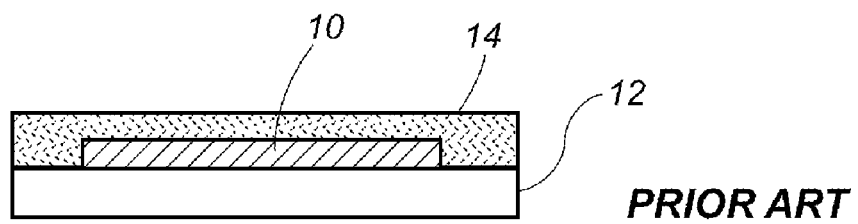
FIG. 2 is a schematic representation of a second step in manufacturing a PRIOR ART hermetic chamber with electrical feedthroughs.
Figure 3:
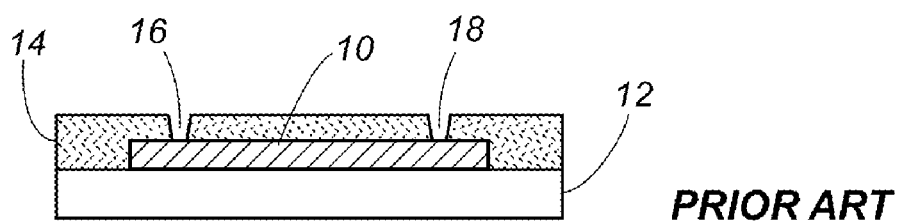
FIG. 3 is a schematic representation of a third step in manufacturing a PRIOR ART hermetic chamber with electrical feedthroughs.
Figure 4:
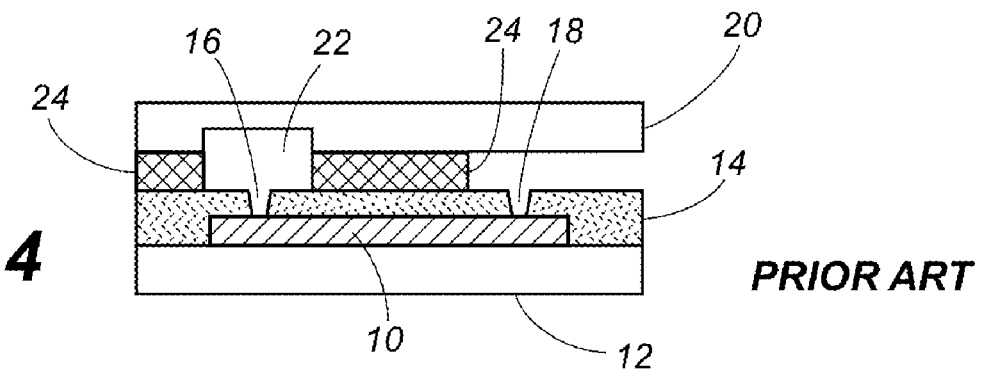
FIG. 4 is a schematic representation of a fourth step in manufacturing a PRIOR ART hermetic chamber with electrical feedthroughs.
Figure 5:
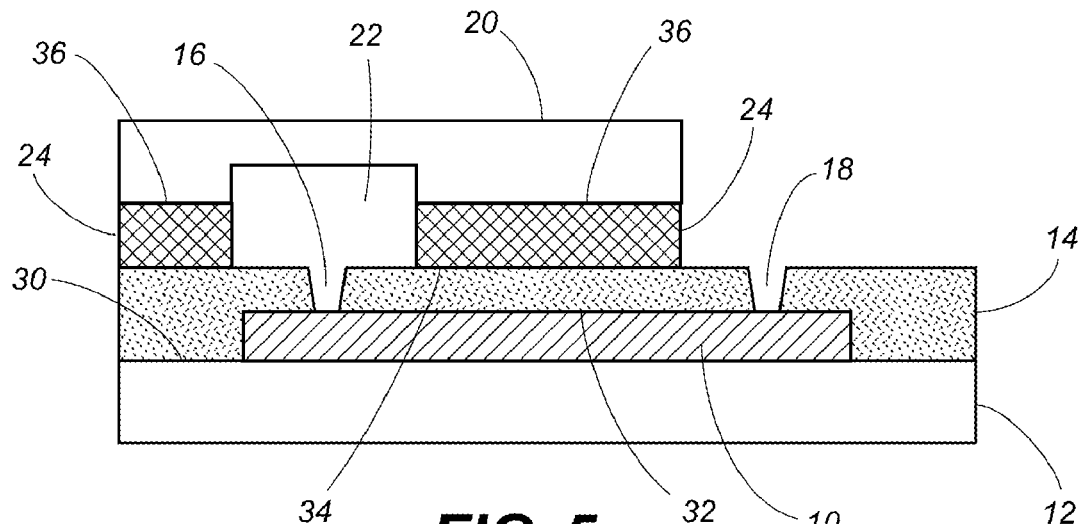
FIG. 5 is a schematic representation of a completed PRIOR ART hermetic chamber with electrical feedthroughs.
Figure 6:
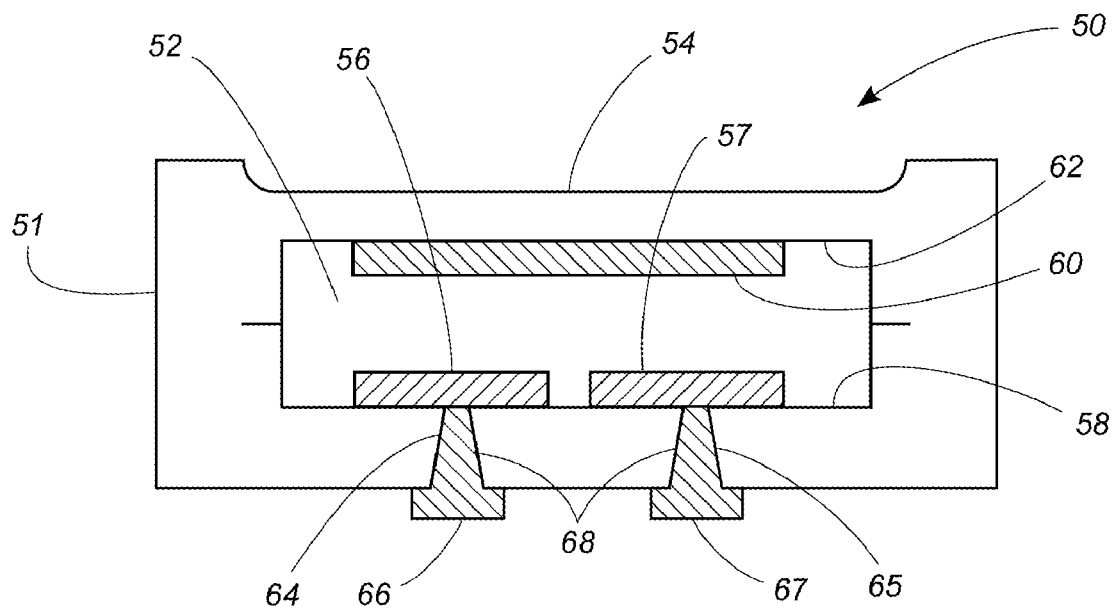
FIG. 6 is a schematic representation of a hermetic chamber with electrical feedthroughs according to a disclosed embodiment of the present invention.

Referring now to the drawings, in which like numerals indicate like elements throughout the several views, FIG. 6 illustrates a sensor 50 that includes a pressure cavity body 51 defining an internal pressure chamber 52. One of the walls defining the pressure cavity 52 comprises a deflectable region 54 configured to deflect under a physiologically relevant range of pressure. In a preferred embodiment, a wall of the pressure cavity body 51 is thinned relative to other walls of the pressure cavity body to form the deflectable region 54. The sensor 50 can be fabricated using micro-machining techniques and is small, accurate, precise, durable, robust, biocompatible, and insensitive to changes in body chemistry or biology. Additionally, the sensor 50 can incorporate radiopaque features to enable fluoroscopic visualization during placement within the body. The sensor 50 is preferably formed using electrically insulating materials, particularly biocompatible ceramics, as substrate materials. Suitable materials are selected from a group comprising glass, fused silica, sapphire, quartz, or silicon. In one embodiment, fused silica is the substrate material.

A capacitor comprises a pair of lower electrodes 56, 57 located on a first wall 58 of the chamber 52. The two lower electrodes 56, 57 are electrically isolated from one another. A third electrode 60 is disposed on an opposite wall 62 of the pressure cavity 52 in parallel, spaced apart relation to the lower electrodes 56, 57. The upper electrode 60 is mechanically coupled to the deflectable region 54. As ambient pressure increases, the deflectable region 54 moves inward, displacing the upper electrode 60 toward the lower electrodes 56, 57, thereby changing the characteristic capacitance value of the capacitor.

The capacitor configuration depicted here is one example where the lower capacitor electrode consists of two electrically isolated regions, 56 and 57, although other configurations are possible and obvious to one skilled in the art.

The lower portion of the pressure cavity 52 comprises passages 64, 65 that traverse the hermetic pressure cavity body 51 and are in contact with the electrodes 56, 57. As shown in FIG. 6, electrical contact pads 66, 67 can be formed on the back side of the electrodes 56, 57 and extend to the exterior of the housing, thereby providing a region on the exterior of the sensor 50 configured with sufficient dimensions so as to allow for a means for connection with external electronics. As an alternative, the passages 64, 65 can be filled with an electrically conductive material, with contact pads 66, 67 in electrical communication with the electrodes 56, 57 by way of the conductive material 68. The electrode 56, the passage 64, and, if present, the electrical contact pad 66 and any electrically conductive material 68 filling the passage 64 comprises a first electrical feedthrough 70. The electrode 57, the passage 65, and, if present, the electrical contact pad 67 and any electrically conductive material 68 filling the passage 65 comprises a second electrical feedthrough 71.

It is a preferred embodiment of this invention that the metal-fused silica interface between the lower electrodes 56, 57 and the interior surface of the pressure cavity body 51 be hermetic. The electrical contact pads 66, 67 can occupy either all or part of the passages 64, 65. A variety of metal deposition techniques can be used (e.g., electroplating, use of molten metal, or PVD) depending on the choice of metal and desired material properties. In the case of a partially-filled feedthrough passage 64, 65, a void inside the feedthrough passages and above the electrical contact pads 66, 67 will remain. In order to fill these voids and to enhance the strength of the feedthroughs 70, 71, any remaining space in the passages 64, 65 can be filled with a ceramic material. Glass frit is one example of a ceramic material that can be used to fill the remaining space and heated sufficiently that the material flows, thereby eliminating any voids in the ceramic material.

In the case of metal-filled feedthrough cavities, the pads 66, 67 on the exterior of the package are formed by, e.g., fusion bonding, low pressure plasma spray, laser welding, electroplating or PVD, depending on the choice of metal and the desired material properties. The electrical contact pads 66, 67 provide a site to connect to external electronics.

Suitable non-refractory metals for the electrical feedthroughs include gold, platinum, nickel, and silver and alloys thereof. Suitable refractory metals include niobium, titanium, tungsten, tantalum, molybdenum, chromium, and a platinum/iridium alloy and alloys thereof. If refractory metals are used to construct the feedthroughs, either alternating or direct current may be used to bias the sensors by external electronics. If any other metals are used, the sensors should be biased under AC power to prevent the onset of bias-induced corrosion.

The pressure cavity 52 is hermetic for the following reasons. First, the pressure cavity body 51 is formed of a hermetic material and is a unitary structure, meaning there are no seams or bi-material joints that can form a potential path for gas or fluid intrusion into the pressure chamber other than the passages 64, 65, which themselves are hermetically sealed. One reason for the hermeticity of the passages 64, 65 is that the electrodes 56, 57 are hermetically imposed onto the wall 58 over the feedthroughs. The electrodes 56, 57 (along with any other metallic structure fixed to the ceramic substrate) optionally form an intermetallic compound. An intermetallic compound is formed between a metal and a substrate when chemical reactions take place that result in the formation of covalent bonds between two or more elements, with at least one of the elements coming from the substrate and one from the metal. Optionally, the material 68 filling the passages 64, 65 is itself capable of hermetic sealing such that the interface between the material 68 and the material defining the feedthrough passages is also hermetic. Thus gas or fluid would have to pass through or around the material 68 in the passages 64, 65 and pass through or around the electrodes 56, 57 before it could enter the pressure chamber and compromise its integrity. And finally, the passages 64, 65 are small, thereby minimizing the area of interface and reducing the probability of flaw creation and propagation. In the disclosed embodiments, the passages have cross-sectional areas ranging from $10^{-6}$ to $10^{-9}$ square meters.

A disclosed method of fabricating the sensor 50 depicted in FIG. 6 is based on the micromachining of two substrates that are subsequently brought into contact and cut into individual sensors. The manufacturing process described herein and illustrated in FIGS. 7-25 comprises a series of etching, deposition and patterning processes to create depressions and electrodes on the surfaces of the substrates. More specifically, a first substrate is subjected to a series of processes to create local depressions of known depth and to deposit and pattern thin film electrode(s) at the bottom of the depressions. Next, a second substrate is subjected to similar processing as the first substrate to create complementing electrode(s) whose overall footprint and in-plane position correspond to the footprint and in-plane position(s) of the electrode(s) on the first substrate. Creation of depressions in the surface of the second substrate is optional and depends on the desired final configuration of the sensor. The first substrate is then subjected to additional processing on the side of the substrate opposite the previously formed electrode(s) to physically remove material through the entire thickness of the substrate to create the passages that are the first step in creating electrically conductive feedthroughs that allow for electrical communication with the hermetic cavity. The configuration of the electrodes and the passages can be altered to provide for a variety of configurations, such modifications providing manufacturing and/or performance advantages. The two substrates are then brought into intimate contact with the electrodes facing one another. The substrates form a temporary bond due to the presence of Van der Waals forces. The electrodes on opposing substrates are separated by a gap of known value, i.e., the difference between the sum of the depths of the recessed region and the sum of the thicknesses of the electrodes. A laser is then used to excise the sensor into its final overall dimensions from the two-substrate stack.

The laser cutting operation fuses the substrates, hermetically sealing the sensor and trapping air or any other desirable gas in the hermetic cavity of the sensor, or creating a vacuum within the hermetic cavity of the sensor. In one example, a $CO_2$ laser operating at a peak wavelength of ten microns is used to hermetically seal and to reduce the sensor to its final size. The laser energy is confined to a precise heat effect zone where the substrates are fused, eliminating any material interface between the original substrates.

The resulting hermetic package presents electrical feedthroughs 70, 71 created in the sensor body 51 that allow for communication between components inside the hermetically-sealed sensor 50 and external electrical components. The feedthroughs 70, 71 are small, thereby minimizing the area of interface. Such feedthroughs interface with the substrate at areas ranging from $10^{-6}$ to $10^{-9}$ square meters.

The manufacturing of the sensor 50 depicted in FIG. 6 from the substrate (a.k.a. wafer) level to the final device is described in greater detail below. For clarity, the manufacture of the sensor 50 is described on a single-sensor basis, although it will be understood that multiple sensors can be created simultaneously on the substrate in a batch process to increase manufacturing efficiency.

The lower substrate is processed to create a recessed region in its surface and thin film electrodes at the bottom surface of each recessed region. Creation of a recessed region with known geometry comprises the steps of (i) depositing and patterning a mask at the surface of the wafer, (ii) etching the wafer material through openings in the mask, and (iii) removal of the mask.

Figure 7:
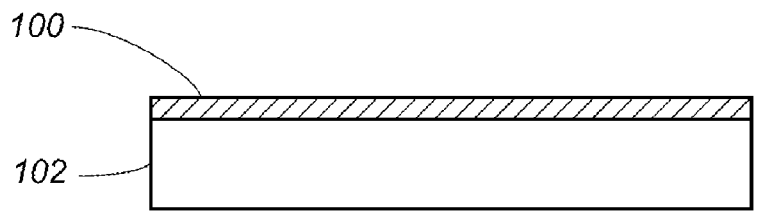
FIGS. 7-25 are schematic representation of the steps in manufacturing the hermetic chamber of FIG. 6.

One method for creating the desired recessed region is depicted in FIGS. 7-20 and described as follows: Referring first to FIG. 7, a thin metallic film 100 is deposited at the surface of a fused silica substrate 102 using a physical vapor deposition system (e.g., an electron-beam evaporator, filament evaporator, or plasma assisted sputterer). This thin film layer 100 will form a mask used to create a recessed region in the upper surface of the substrate 102. The nature and thickness of the metal layer 100 are chosen so that the mask is not altered or destroyed by a glass etchant. For the purpose of illustration, Cr/Au or Cr/Ni are examples of suitable mask materials. A representative Cr/Au mask is 100-200 Angstroms of chromium and 1000-3000 Angstroms of gold.

Figure 8:
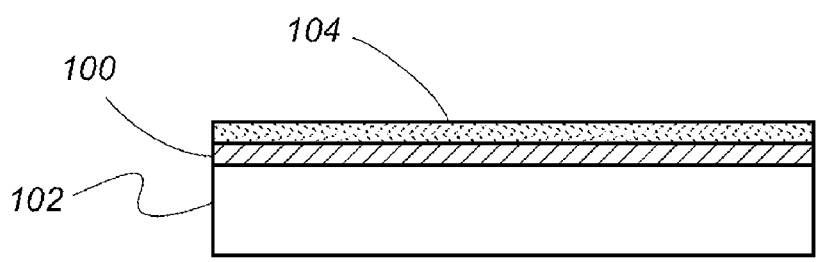
Figure 9:
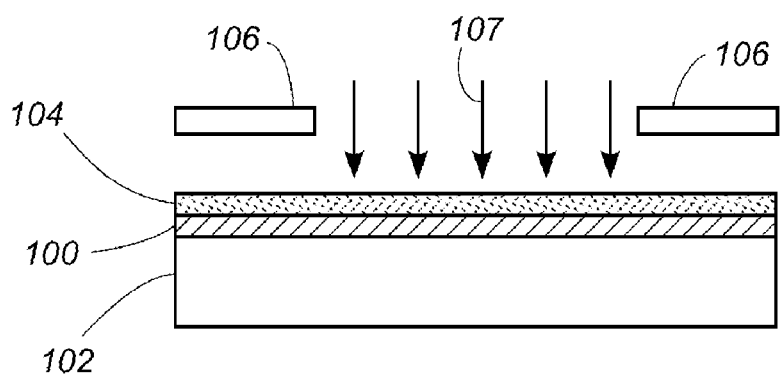
Figure 10:
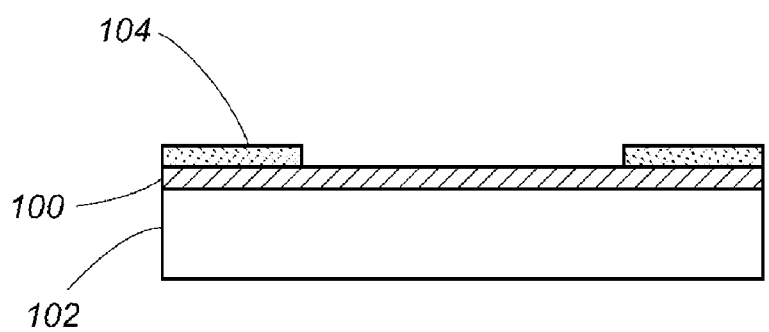

As can be seen in FIG. 8, a layer 104 of photoresist is formed atop the thin metal film 100 and substrate 102. Then, as shown in FIG. 9, a mask 106 having a rectangular opening is positioned over the photoresist layer 104, and ultraviolet light, indicated by the arrows 107, is directed through the mask 106 onto the exposed portions of the photoresist layer 104. The exposed photoresist defining the body of the rectangular region is removed via the appropriate etchants, as illustrated in FIG. 10.

Figure 11:
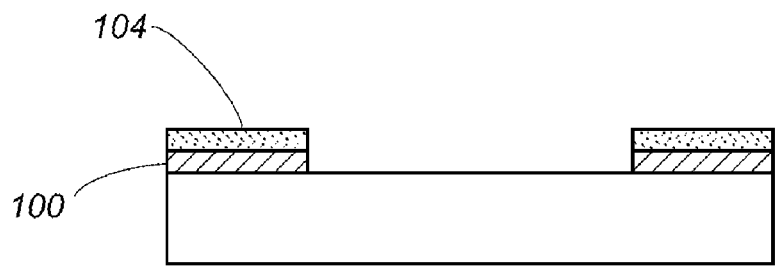
Figure 12:
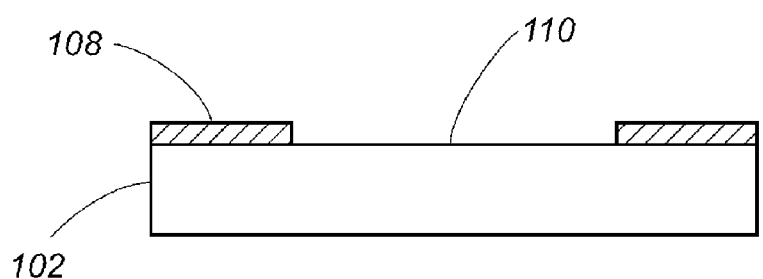

Referring now to FIG. 11, etchants are used to etch away the rectangular portion of the thin metallic film 100 exposed through the patterned photoresist layer 104. When the remaining photoresist material is removed, such as by using an appropriate organic solvent, the substrate 102 is left with a metallic mask 108 defining a rectangle 110, as illustrated in FIG. 12.

Figure 13:
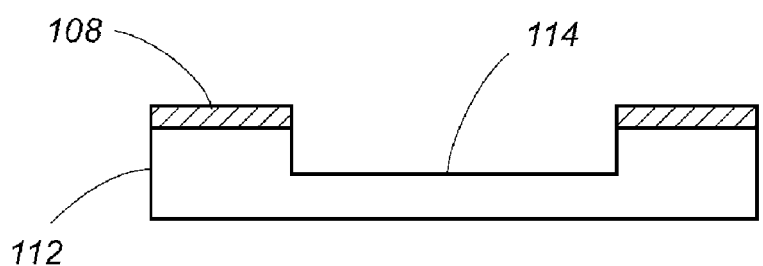
Figure 14:
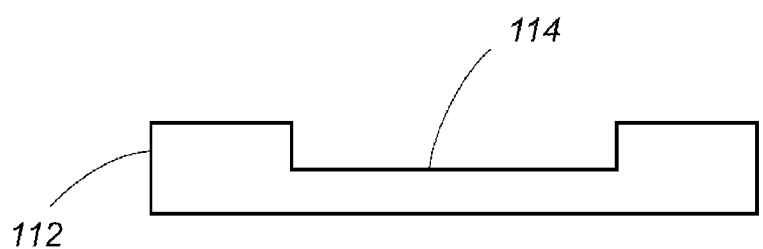

A glass etchant is now used to etch the portion of the upper surface of the substrate 102 that is exposed through the mask 108. To accomplish this, the substrate 102 is placed in a fixture that prevents the etchant from contacting the un-masked back side of the substrate and is then submerged in a solution containing hydro-fluoric acid, resulting in etching of the masked substrate only where the fused silica is exposed. The substrate 102 is removed from the acid when the substrate has been etched to the desired depth, usually on the order of 1-3 micrometers. The resulting etched substrate 112 with rectangular recessed region 114 is shown in FIG. 13. Then, as shown in FIG. 14, the mask 108 is removed from the etched substrate 112 using proper selective etchants and solvents.

Figure 15:
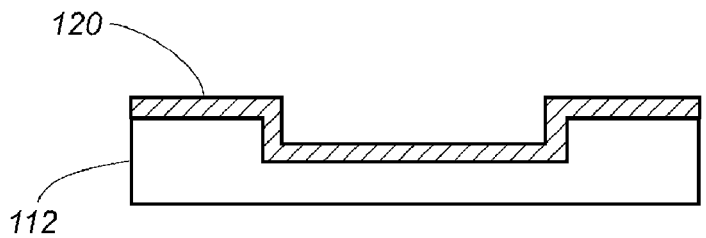

The etched substrate 112 is now primed for creation of electrodes at the bottom of the recessed region 114. As shown in FIG. 15, a thin film metal layer 120 is deposited onto the upper surface of the etched substrate 112. For the purposes of illustration, this thin film metal layer 120 can be composed of elemental chromium and gold. A representative Cr/Au layer is a 100-200 Angstrom seed layer of chromium and 1000-3000 Angstroms of gold. The thin film layer 120 can also utilize a Ti seed layer and either a Ni or Pt secondary layer. The thickness of this layer is carefully controlled so that, in this embodiment, the metal layer 120 does not protrude above the level of the original surface of the patterned side of the substrate.

Figure 16:
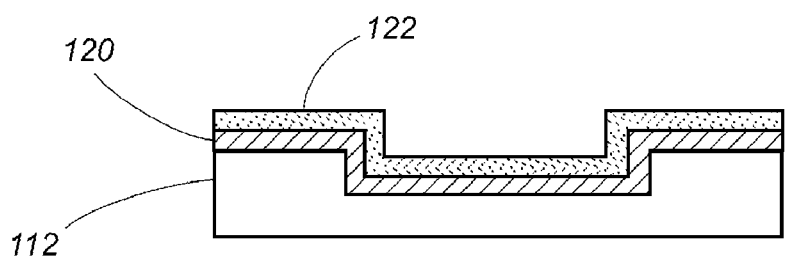
Figure 17:
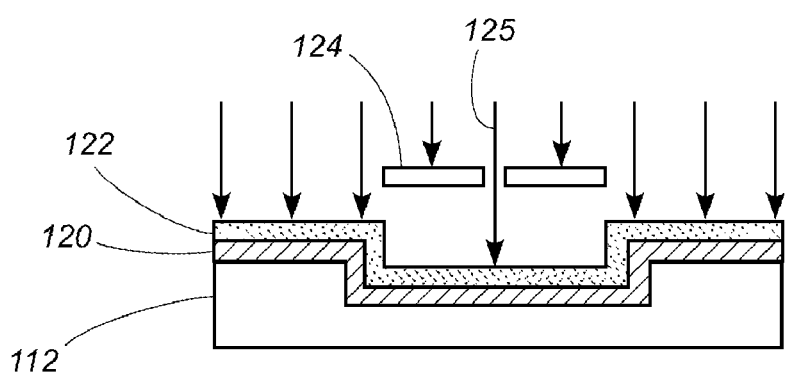
Figure 18:
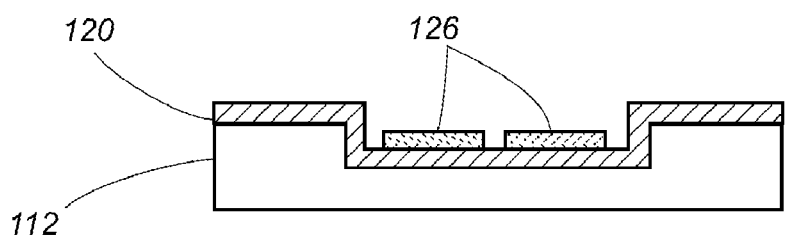

Referring now to FIG. 16, a layer of photoresist 122 is deposited over the surface of the metal layer 120. A mask 124 is positioned over the photoresist layer 122, and ultraviolet light, indicated by the arrows 125, is directed onto the exposed portions of the photoresist layer, as shown in FIG. 17. Then, as illustrated in FIG. 18, the exposed photoresist is removed, leaving a mask 126 of photoresist material formed on the upper surface of the metal layer 120.

Figure 19:
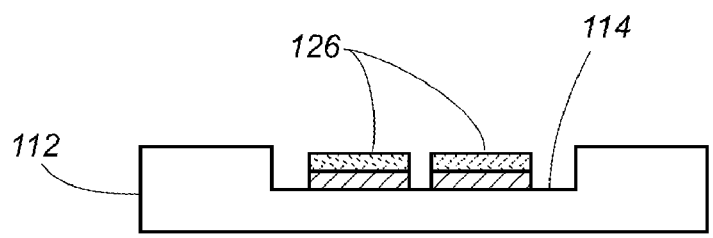

Next, the portions of the metal layer 120 exposed through the mask 126 are etched away, as illustrated in FIG. 19. In this instance, the patterns defined by the remaining photoresist 126 represent two side-by-side rectangles whose in-plane, overall foot print is smaller than that of the recessed region 114. The rectangles are a few micrometers to tens of micrometers apart and maintain at least a few micrometers wide border separating the rectangles from the perimeter of the rectangular trench 114. Subsequently, the photoresist mask 126 is removed with appropriate organic solvents.

Figure 20:
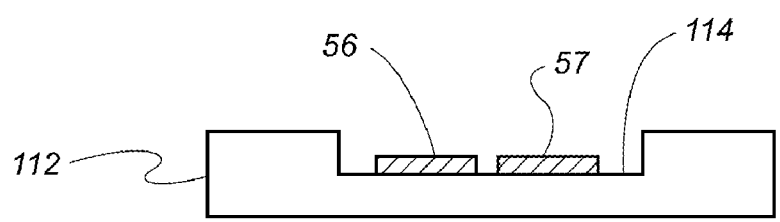

At this point, as depicted in FIG. 20, the etched lower substrate 112 is patterned with a rectangular trench 114 etched into its upper surface, and the base of the rectangular trench contains side-by-side, spaced apart metal electrodes 56 and 57 of known thickness. The difference between the height of the upper surface of either electrode, $H_1$, and depth $D_1$ of the trench 114 created in the lower substrate 102, is substantially constant (excepting for inherent variations in the substrate and patterned metal), and these dimensions are known with great precision, i.e. fractions of micrometers.

An optional step involving creation of an intermetallic compound can be performed, e.g., at this step and serves to increase the hermeticity of the metal-substrate interface. An intermetallic compound is created by annealing a metal deposited onto a ceramic substrate at a temperature sufficient to initiate covalent bonding across the substrates. It may be necessary to protect the surface of the metal from oxidation by providing a protective layer to the exposed metal or by performing the annealing step in an inert environment (e.g., vacuum, $N_2$). One example of an intermetallic compound is the Ti—O—Si system, where titanium is deposited onto a $SiO_2$ substrate. The exposed Ti surfaces are protected from oxidation by a layer of silicon nitride. The metal and underlying ceramic substrate are heated at a ramp rate of, e.g., 4-10 degrees C./minute to between substantially 700 and substantially 1100 degrees C. in order to drive the fusion reaction. The temperature is gradually increased and decreased in order to obviate any potential problems with CTE mismatch between the metal and the substrate. If necessary, the protective layer is then removed. In this Ti—O—Si system, either the Ti dissolves significant amounts of oxygen prior to oxide formation enabling the oxygen to react with Si diffusing to the interface, or the stable oxide evolves from TiO to $SiO_2$ in the presence of the Ti-rich phases. Other configurations of metals and substrates can be used to achieve the same effect, e.g., W—Si—O, Mo—Si—O, Ta—Si—O, and Ti—Si—N. To carry out this annealing step, one skilled in the art need only reference the ternary phase diagram to determine sufficient annealing temperatures and to discern the relevant properties of the intermetallic compound.

Figure 21:
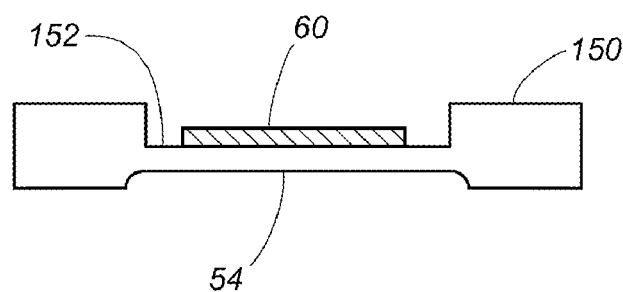

Referring now to FIG. 21, an upper substrate 150 is micro-machined using the same sequence of steps described above to create a rectangular trench 152 in the fused silica, and the electrode 60 is created using the same photolithographic process as those described for the lower substrate 102. The only change to the preparation of the upper substrate is in the pattern transferred to the second layer of photoresist, i.e. the photoresist layer that serves as a mask for creating the metal electrode. On this substrate 150, one continuous rectangle is patterned that maintains a border at least one micrometer thick separating the electrode 60 from the perimeter of the rectangular trench 152.

As an optional preparatory step for the upper substrate 150, a blanket etch can be performed on the back side using hydrofluoric acid or any other suitable etchant to form the recess 54 such that overall thickness of the substrate 150 is reduced to a known thickness that lies in the range of 30-100 micrometers. This step serves to increase sensitivity of the deflectable region of the pressure cavity body 51 (FIG. 6). Alternatively, the upper substrate can have an initial thickness in this range, which obviates the need for the above-described step.

Figure 22:
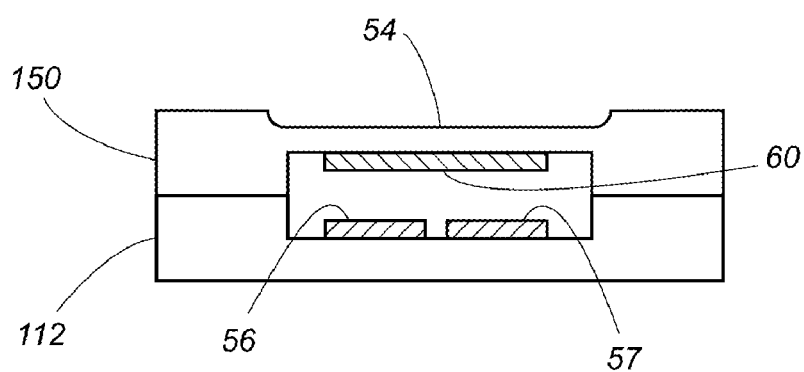
Figure 23:
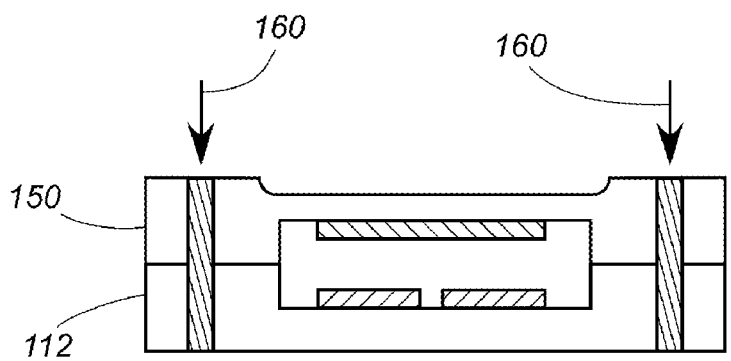
Figure 24:
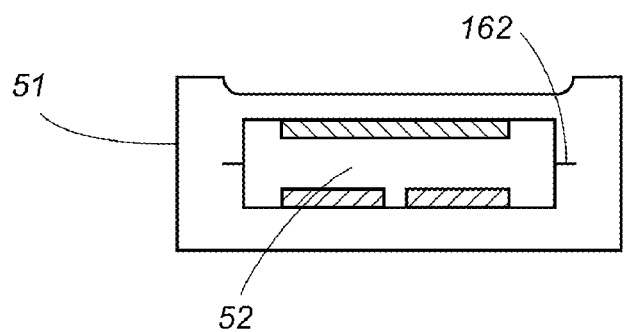

The substrates 112, 150 are then aligned, subjected to bonding, and reduced to the final overall dimension of the sensor as shown in FIG. 6 according to the following description: Both the upper and lower substrates 112, 150 are prepared for assembly, e.g., by cleaning. The patterned surfaces of the substrates are faced and aligned so that the corresponding rectangular trenches 114, 152 created in each substrate are positioned directly on top of one another. The two substrates 112, 150 are brought together and placed in intimate physical contact, as shown in FIG. 22. A temporary bond is formed because of Van der Waals forces existing between the two substrates. As previously described, a gap is maintained between the electrodes 56, 57 and the electrode 60 where the distance between the electrodes is precisely known. Referring to FIG. 23, using a $CO_2$ laser, indicated by the arrows 160, the sensor is reduced to its final dimensions. The laser cutting process also seamlessly fuses the upper and lower substrates 112, 150. The result of the above steps is depicted in FIG. 24. Thus, the rectangular electrodes created combine to form a complete device that displays the electrical attributes of a parallel plate capacitor.

With further reference to FIG. 24, the power of the $CO_2$ laser is controlled such that heat damage to the internal components is avoided. Consequently it is possible that some vestige of a seam 162 may remain between the upper and lower substrates 112, 150. So long as the outer periphery of the pressure cavity body 51 is completely fused, the interior chamber 52 will be hermetic.

Figure 25:
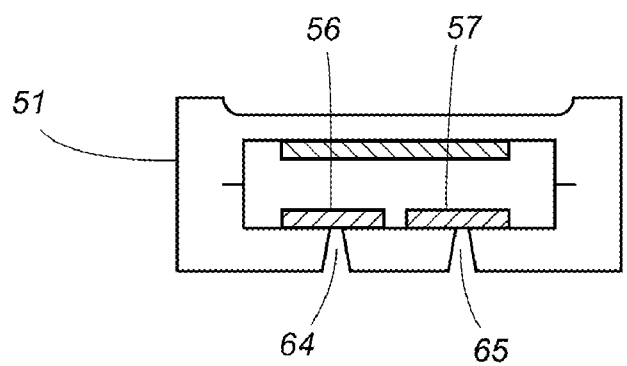

At some point, the feedthrough passages 64, 65 are created by removing material on the lower surface of the pressure cavity body 51 to expose the back side of the capacitor electrodes 56, 57, establishing electrical communication through this location as pictured in FIG. 25. This process step can take place after completion of the electrodes 56, 57 on a single substrate 112, after the two substrates 112, 150 have been temporarily bonded, or after the sensors 50 have been individualized, depending on manufacturing considerations. Either laser ablation or chemical etching or a combination of the two is performed to remove the glass substrate and to expose a portion of the back side of each of the electrodes 56, 57 located on the lower surface of the pressure cavity 51. In order to provide for electrical contact pads, any number of techniques can be used to deposit a layer of metal into the passages 64, 65. The metal choice and deposition technique cannot be chosen independently from one another, but these combinations, along with their respective advantages and shortcoming, are well-known in the art. For purposes of illustration, techniques such as low-pressure plasma spray, electroplating, or screen printing can be utilized to this end. Optionally, if compatible with the deposition technique chosen and the strength of the exposed electrodes, the metal deposition is performed under vacuum. If the feedthrough passages 64, 65 are only partially filled with the electrical contact pad, a ceramic material (e.g., glass frit) can be used to fill the remainder. This would provide mechanical reinforcement to the feedthrough structure.

It is a further aspect of this invention to provide for a hermetic sensor that incorporates a pressure cavity and additional electrical components that incorporate the above described advantages, with additional functionality and advantages being provided. A sensor according to the invention, along with desirable modifications, is depicted in FIG. 26 and is further described below.

Figure 26:
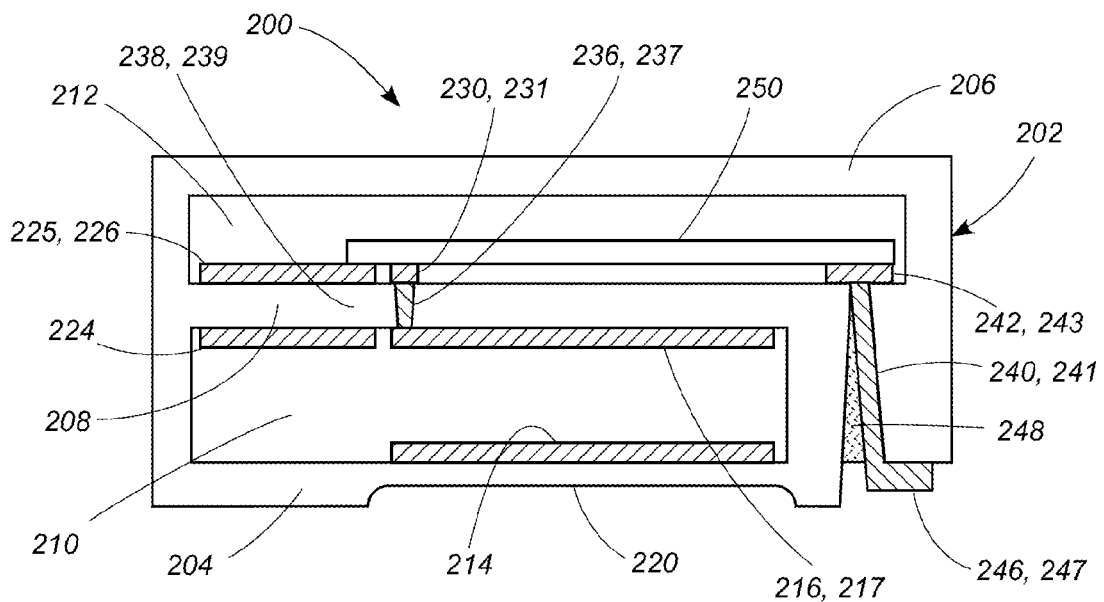
FIG. 26 is a schematic representation of a hermetic chamber with electrical feedthroughs according to a second disclosed embodiment of the present invention.

FIG. 26 shows a sensor 200 comprising a sensor body 202 of fused silica or other suitable material, as discussed above. The sensor body 202 comprises a lower wall 204, an upper wall 206, and an intermediate wall 208. The intermediate wall 208 divides the hollow interior of the sensor body 202 into a lower hermetic chamber (a.k.a. pressure chamber) 210 and an upper chamber 212. A first electrode 214 is affixed within the lower hermetic chamber 210 to the lower sensor body wall 204. A second electrode 216 is affixed within the lower hermetic chamber 210 to the intermediate wall 208. A third electrode 217 is behind and in-plane with the second electrode 216 and is thus not visible in FIG. 26. The first electrode 214 is thus arranged in parallel, spaced-apart relation with respect to the second and third electrodes 216, 217 so as to form a gap capacitor. A recess is formed in the lower sensor body wall 204, or the substrate comprising the lower sensor body wall is configured to be sufficiently thin, to form a region 220 that will deflect in response to pressure changes. Because the first electrode 214 is coupled to the deflectable region 220, the distance between the first electrode 214 changes with respect to the second and third electrodes 216, 217 with variations in external pressure. Thus the characteristic capacitance of a capacitor comprising the first, second, and third electrodes 214, 216, 217 changes with movement of the deflectable region 220.

Also mounted to the intermediate wall 208 within the lower hermetic chamber 210 is a fourth electrode 224. A fifth electrode 226 is located on the intermediate wall 208 within the upper chamber 212, which is, optionally, hermetic. A sixth electrode 225 is behind and in-plane with the fifth electrode 226 and is thus not visible in FIG. 26. The fourth electrode 224 is disposed in parallel, spaced apart relation with respect to the fifth and sixth electrodes 225, 226, separated by the thickness of the intermediate wall 208. Because the distance between the fourth electrode 224 and the fifth and sixth electrodes 225, 226 remains constant, a capacitive circuit comprising the fourth, fifth, and sixth electrodes provides a fixed reference. In the capacitor configuration described above, an example where the need for feedthroughs into the lower hermetic chamber 210 is eliminated, a capacitor configuration (i.e., a configuration that is physically two capacitors in parallel) that sacrifices capacitance value for ease of manufacture is utilized. Alternative configurations can be provided for, require either one or two feedthroughs into the lower hermetic chamber and are obvious to one skilled in the art.

Electrical contact pads 230, 231 are formed on the intermediate wall 208 within the upper hermetic chamber. A first pad 230 is located opposite a portion of the second electrode 216. A second pad 231 is located opposite a portion of the third electrode 217 and is behind and in plane with the first pad 230 and thus not visible in FIG. 26. A first feedthrough passage 236 places the first pad 230 and the second electrode 216 in communication through the intermediate wall 208. A second feedthrough passage 237 places the second pad 231 and the third electrode 217 in communication through the intermediate wall 208. The electrical feedthroughs 236, 237 are filled with a conductive material, such as metal. The second and third electrodes 216, 217 are hermetically imposed against the openings of the passages 236, 237. Optionally, the pads 230, 231 and the medium filling the passages 236, 237 are hermetic and are hermetically imposed against the openings of the feedthrough passages 236, 237. At a minimum, this hermetic imposition of electrodes 216 and 217 renders the feedthroughs hermetic. Optionally, electrical contact pads 230, 231 and/or the material filling the feedthrough passages 236, 237 further renders the feedthroughs hermetic.

To provide electrical access to the interior of the sensor, fifth and sixth feedthrough passages 240, 241 are provided. The passage 240 extends from the exterior of the sensor body to the upper chamber 212. The passage 241 also extends from the exterior of the sensor body to the upper chamber 212 but is behind and in plane with the electrical feedthrough 240 and thus not visible in FIG. 26. An electrical contact pad 242 is located within the upper chamber 212 on the intermediate wall 208 and is imposed over the passage 240. Likewise, an electrical contact pad 243 is located within the upper chamber 212 on the intermediate wall 208 and is imposed over the passage 241. The electrical contact pad 243 is behind and in plane with the electrical contact pad 242 and is therefore not visible in FIG. 26. Electrical contact pads 242, 243 can be configured to provide a hermetic interface with the intermediate wall 208. In the embodiment of FIG. 26, the passages 240, 241 are partially filled with a conductive material such as gold, and electrical connection can be made on the exterior of the sensor body 202 as described in previous examples. Any remaining voids in the passages 240, 241 are filled with a material 248 such as glass frit, which fills the space not occupied by the conductive material and enhances the mechanical stability of the feedthrough structure. Optionally, hermetic imposition of the conductive material into the passages 240, 241 further renders the feedthroughs hermetic.

The upper chamber 212 contains one or more electrical components such as a silicon chip 250 bearing electronics that can act to buffer, to linearize, or otherwise to manipulate the electronic signal from the transducer. The silicon chip 250 is placed in electrical communication with the electrodes and with an external source by way of the conductive pads 230, 231, 242, and 243. In one embodiment (not shown), the electronics comprises an A/D converter placed in series with an additional silicon chip bearing electronics. In this case, an additional set of electrical contact pads are provided that allow electrical communication between the A/D converter and the additional electronics.

The fabrication of the sensor depicted in FIG. 26 is based on the micromachining of three substrates that are subsequently brought into contact and cut into individual sensors. The fabrication of the individual substrates as well as their final assembly is described as follows: The thin metal electrodes 216, 217 having overall, in-plane dimensions of 500 micrometers width, 3-4 mm length and 500 nm thickness, are formed within a recessed region of the same dimensions of the electrode that was previously etched into the surface of a first substrate using photolithography and chemical etching as described for previous examples. The metal electrodes are shorter than the depth of the recessed region by 200 nm. A second substrate has a second recessed region formed therein having a depth of 700 nm and the same cross-sectional dimensions as the recessed region in the upper wafer. A thin metal electrode 214, having a thickness of 500 nm and the same overall, in-plane dimensions as electrodes 216 and 217, is then formed into this recessed region. The electrode 214 is thinner than the depth of the recessed region by 200 nm. When the first and second substrates are bonded together with their respective recessed regions facing each other, a gap of 400 nm is thereby formed between the electrode 214 and the electrodes 216 and 217. Feedthrough passages 236, 237 are then created from the top surface of the second substrate down to the upper electrodes 216 and 217, using laser rastering and HF etching. Also, electrode 224 and electrodes 225, 226 are formed on opposite sides of the wall 208.

Conductive pads 230, 231, 242, and 243 on the top surface of the second substrate can be formed during the feedthrough fabrication sequence. The silicon chip 250 is then connected to the conductive pads 230, 231, 242, and 243 that were formed during the feedthrough fabrication sequence. A third substrate that has a recess sufficiently deep to contain the silicon chip 250 and to make contact to the second substrate is added to the assembly. A laser is then used to remove material around the sensor periphery to reduce the sensor to final dimensions. In the disclosed embodiment, the sensor is 750 micrometers wide by 4-5 mm long and 0.6 mm tall. Passages 240 and 241 are then created to allow for conductive communication with external electronics.

In an alternative example, a piezoresistive transduction scheme can be utilized to measure changes in the position of the deflectable region in the pressure cavity. One or more piezoresistive elements translate mechanical strain into changes in electrical resistance. The piezoresistor is made of, e.g., polysilicon and formed on the interior of the pressure cavity in lieu of the electrodes in previous examples. The resistance modulation is, e.g., detected through a fully active Wheatstone bridge, as is known in the art. Optimally, the Wheatstone bridge configuration used is one where only one leg of the bridge is fixed to the deflectable region of the pressure cavity. This design reduces the number of feedthroughs to two.

Figure 27:
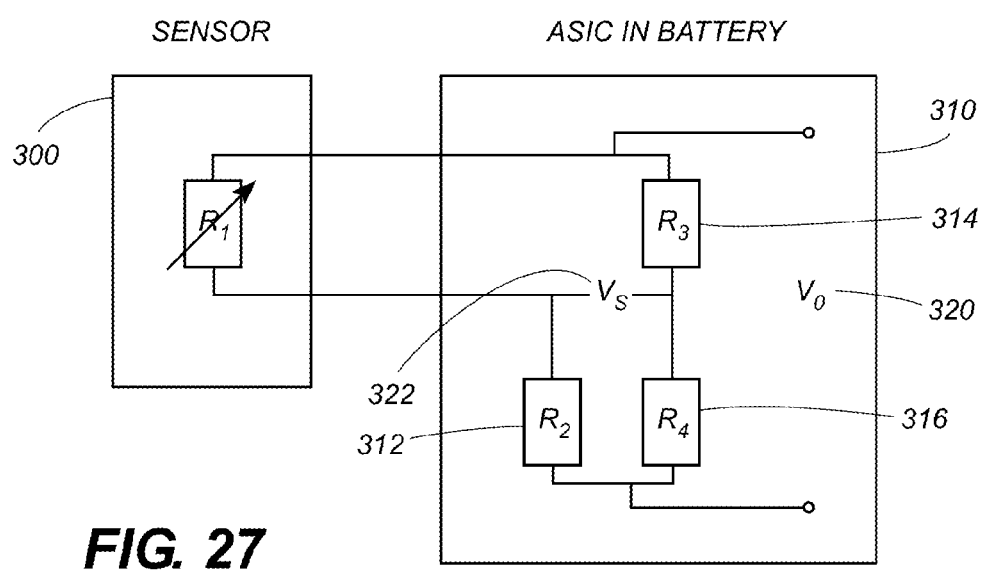
FIG. 27 is an electrical schematic of a piezoresistive transduction scheme for measuring changes in the position of the deflectable region in the pressure cavity of the hermetic chambers of FIGS. 6 and 26.

One proposed transduction scheme capable of measuring changes in the position of the deflectable region in the pressure cavity is illustrated in FIG. 27. Sensor 300 and ASIC 310 together comprise an active Wheatstone bridge, which is known in the art for measuring an unknown resistance. Sensor 300 comprises a piezoresistor of resistance value R1. Piezoresistors are well known in the art. The other three legs of the Wheatstone bridge comprise resistors 312, 314, and 316 with values R2, R3, and R4 respectively. Voltage 320 of value V0 is supplied by a battery (not shown). The circuit operates on the following principle, which discussion is presented for illustrative purposes only. When voltage 320 is applied with value V0, and R1, R2, R3 and R4 are all of known values, then the value VS of voltage 322 may be determined as is well known in the art from knowledge of V0, R1, R2, R3, and R4. However, if the resistance R1 of sensor 300 changes while values R2, R3, and R4 of resistors 312, 314, and 316 remain unchanged, then the value VS of voltage 322 will change. As is well known in the art, measurement of the changed value VS of voltage 322 may then be used to determine the value of resistance R1 of the sensor 300. Because sensor 300 comprises a piezoresistor, the value R1 of sensor 300 changes in response to a change in position of the deflectable region in the pressure cavity, and this circuit therefore gives a measurement of that change in position.

Figure 28:
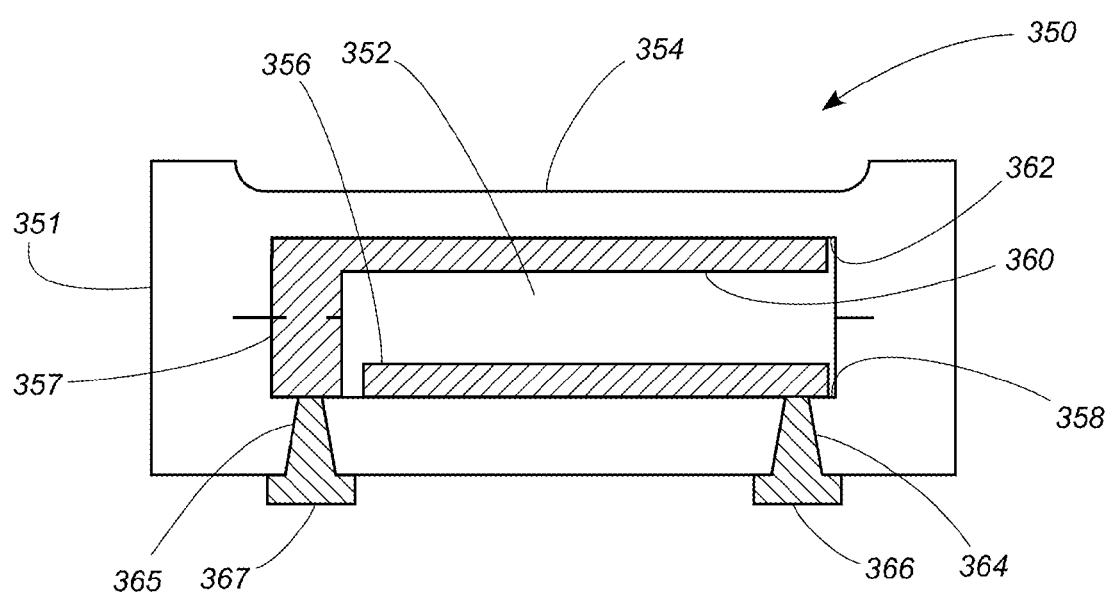
FIG. 28 is a schematic representation of a hermetic chamber with electrical feedthroughs according to a third disclosed embodiment of the present invention.

As previously indicated, various capacitor configurations are possible. FIG. 28 illustrates a sensor 350 that includes a pressure cavity body 351 defining an internal pressure chamber 352. One of the walls defining the pressure cavity 352 comprises a deflectable region 354 configured to deflect under a physiologically relevant range of pressure. In a preferred embodiment, a wall of the pressure cavity 351 is thinned relative to other walls of the pressure cavity body to form the deflectable region 354.

A capacitor comprises a single lower electrode 356 located on a first wall 358 of the chamber 352. A second electrode 360 is disposed on an opposite wall 362 of the pressure cavity 352 in parallel, spaced apart relation to the lower electrode 356. The upper electrode 360 is mechanically coupled to the deflectable region 354.

The lower portion of the pressure cavity 352 contains a pair of passages 364, 365 that traverse the hermetic pressure cavity body 351. The first passage 364 is in contact with the lower electrode 356. The second passage 365 is in contact with the upper electrode 360 by way of an electrode in the form of an electrically conductive post 357 disposed within the pressure cavity 352. Electrical contact pads 366, 367 are formed within the passages 364, 365 on the back side of the electrodes 356, 357 and extend to the exterior of the housing 351, thereby providing a region on the exterior of the sensor 350 configured with sufficient dimensions so as to allow for a means for connection with external electronics.

While the invention as been illustrated in the context of a biological device, it will be appreciated that the hermetic chamber herein described can be adapted to non-biological applications, for example, industrial applications in which a harsh environment is encountered.

Specific embodiments have been described herein, by way of example and for clarity of understanding, and variations and modifications to the present invention may be possible given the disclosure above. Hence the scope of the present invention is limited solely by the appended claims.

What is claimed is:

1. A device comprising:
    a housing having walls defining a chamber, a first one of said walls defining said chamber comprising an exterior wall of said housing;
    a passage through said first one of said walls placing the chamber of said housing in communication with the ambient; and an electrode hermetically imposed over said passage within said chamber of said housing, whereby said passage is hermetically sealed;

whereby said chamber is hermetically sealed; and whereby an external electrical device can be placed in electrical communication with said electrode through said passage.

2. The device of claim 1, wherein said housing further comprises a unitary housing.

3. The device of claim 1, wherein said housing is comprised of a ceramic material.

4. The device of claim 3, wherein said housing is comprised of glass, fused silica, sapphire, quartz or silicon.

5. The device of claim 4, wherein the housing is comprised of fused silica.

6. The device of claim 1, wherein said passage has a surface area of from $10^{-6}$ to $10^{-12}$ meters$^2$.

7. The device of claim 6, wherein said passage has a surface area of from $10^{-6}$ to $10^{-9}$ meters$^2$.

8. The device of claim 1, wherein said housing has a volume of from $10^{-8}$ to $10^{-15}$ meters$^3$.

9. The device of claim 1, wherein said passage comprises a first passage, and wherein said device further comprises:

a second passage through said first one of said walls defining said chamber placing said chamber of said housing in communication with the ambient; and a second electrode hermetically imposed over said second passage within said chamber, whereby said second passage is hermetically sealed;

whereby said chamber is hermetically sealed; and whereby a second electrical feedthrough can be placed in electrical communication with said second electrode through said second passage.

10. The device of claim 9, wherein a second one of said walls defining said chamber and opposite said first wall comprises an exterior wall of said housing;

wherein said second one of said walls defining said chamber comprises a deflectable region;

wherein a third electrode is deposited on said second one of said walls within said chamber in said deflectable region; and wherein said third electrode is placed in electrical communication with one of said first electrode or said second electrode.

11. The device of claim 9, wherein one of said first or second electrodes and said third electrode comprise a capacitor.

12. The device of claim 9, wherein a third electrode is deposited on an interior wall of said chamber opposite to said first wall;

wherein said first, second, and third electrodes are electrically isolated from one another; and wherein said interior wall of said chamber opposite to said first wall further comprises a deflectable region.

13. The device of claim 12, wherein said first, second, and third electrodes comprise a capacitor.

14. The device of claim 9, wherein a second one of said walls defining said chamber and opposite said first wall comprises an exterior wall of said housing;

wherein said second one of said walls defining said chamber comprises a deflectable region;

wherein at least one piezoresistor is deposited on said second one of said walls defining said chamber in said deflectable region thereof, wherein said first electrode is in electrical contact with a first side of said piezoresistor; and wherein said second electrode is in electrical contact with a second side of said piezoresistor.

15. The device of claim 1, wherein said passage is partially filled with an electrically conductive material such that said electrically conductive material is in electrical contact with said electrode.

16. The device of claim 15, wherein the remainder of said passage is filled with a different material.

17. The device of claim 16, wherein said different material comprises a ceramic.

18. The device of claim 15, wherein said electrically conductive material is hermetic and is hermetically disposed in said passage.

19. The device of claim 15, wherein said electrically conductive material is selected from the group consisting of gold, platinum, nickel, and silver and alloys thereof.

20. The device of claim 1, wherein said passage is completely filled with an electrically conductive material, whereby an external electrical device can be placed in electrical communication with said electrode by electrically connecting said electrical device to said electrically conductive material.

21. The device of claim 20, wherein said electrically conductive material is hermetic and is hermetically disposed in said passage.

22. The device of claim 20, wherein said electrically conductive material is selected from the group consisting of gold, platinum, nickel, and silver and alloys thereof.

23. A device comprising:

a unitary housing having walls defining first and second internal chambers, said first and second chambers having a common wall;

a passage through said common wall; and an electrode within said first chamber hermetically imposed over said passage, whereby said passage is hermetically sealed;

whereby said first chamber is hermetically sealed from said second chamber; and whereby said second chamber can be placed in electrical communication with said electrode through said passage.

24. The device of claim 23, wherein said passage comprises a first passage, wherein said electrode comprises a first electrode, and wherein said device further comprises:

a second passage through said common wall; and a second electrode within said first chamber hermetically imposed over said second passage.

25. The device of claim 24, wherein said second chamber is at least partially defined by an exterior wall of said unitary housing, and wherein said device further comprises:

a third passage through said exterior wall; and a third electrode within said second chamber imposed across said third passage;

whereby an external electrical device can be placed in electrical communication with said third electrode through said third passage.

26. The device of claim 25, further comprising:

a fourth passage through said exterior wall;

a fourth electrode within said second chamber imposed across said fourth passage, whereby an external electrical device can be placed in electrical communication with said fourth electrode through said fourth passage.

27. The device of claim 26, wherein said third and fourth electrodes comprise hermetic material which is hermetically imposed over said third and fourth passages.

28. The device of claim 25, further comprising an electrical circuit disposed within said second chamber and in electrical communication with said first and second electrodes, said electrical circuit being operable to manipulate an electrical signal input through said first and second electrodes.

29. The device of claim 28, wherein said electrical circuit being operable to manipulate an electrical signal input through said first and second electrodes comprises an integrated circuit.

30. The device of claim 29, wherein said integrated circuit is operable to condition an electrical signal passing between said first and second electrodes.

31. The device of claim 29, wherein said integrated circuit is operable to condition an electrical signal passing between said first and second electrodes and external electronics.

32. A device comprising:
a substrate having first and second sides;
a passage through said substrate from said first side to said second side; and
an electrode hermetically imposed against said first side of said substrate over said passage;
whereby an electrical device on the second side of said substrate can be placed in electrical communication with said electrode on said first side of said substrate through said passage.

33. The device of claim 32, further comprising a conductive material located within said passage and in electrical contact with said electrode, whereby an electrical device on the second side of said substrate can be placed in electrical communication with said electrode on said first side of said substrate through said conductive material.

* * * * *